United States Patent
Livingston

(10) Patent No.: US 8,409,620 B2
(45) Date of Patent: Apr. 2, 2013

(54) SOLID MOSS CONTROL COMPOSITION

(76) Inventor: David W. Livingston, Julian, PA (US)

( * ) Notice: Subject to any disclaimer, the term of this patent is extended or adjusted under 35 U.S.C. 154(b) by 0 days.

(21) Appl. No.: 13/584,910

(22) Filed: Aug. 14, 2012

(65) Prior Publication Data

US 2012/0309624 A1 Dec. 6, 2012

Related U.S. Application Data

(63) Continuation of application No. 12/169,314, filed on Jul. 8, 2008, now abandoned, which is a continuation-in-part of application No. 09/532,687, filed on Mar. 22, 2000, now Pat. No. 7,396,081.

(51) Int. Cl.
- *A61K 9/16* (2006.01)
- *A01N 59/06* (2006.01)
- *A01N 59/16* (2006.01)
- *C05C 9/00* (2006.01)

(52) U.S. Cl. ........ 424/490; 424/496; 424/497; 424/498; 504/121; 504/153; 71/28

(58) Field of Classification Search ........................ None
See application file for complete search history.

(56) References Cited

U.S. PATENT DOCUMENTS

| | | | |
|---|---|---|---|
| 3,964,893 A | 6/1976 | Everingham et al. | |
| 4,214,888 A | 7/1980 | Young | |
| 4,276,732 A | 7/1981 | Nielsen | |
| 4,297,130 A | 10/1981 | Moore, Jr. | |
| 4,507,142 A | 3/1985 | Pace et al. | |
| 4,936,898 A | 6/1990 | Nielsen | |
| 5,009,700 A | 4/1991 | Rothgery | |
| 5,021,247 A | 6/1991 | Moore | |
| 5,108,481 A | 4/1992 | Shutt | |
| 5,139,561 A | 8/1992 | Talbot et al. | |
| 5,589,229 A | 12/1996 | Howard | |
| 6,458,747 B1 * | 10/2002 | Kulik | 504/140 |
| 7,396,801 B1 | 7/2008 | Livingston | |

OTHER PUBLICATIONS

Happ, Keith A., "Moss Eradication in Putting Green Turf", USGA Green Section Record, Sep./Oct. 1998.

* cited by examiner

*Primary Examiner* — Alton Pryor

(74) *Attorney, Agent, or Firm* — Woodard, Emhardt, Moriarty, McNett & Henry LLP

(57) ABSTRACT

A method of controlling moss by applying to grass infested with moss a dry composition including: a) a source of nitrogen such as isobutylenediurea or methylene urea; b) a non-ionic surfactant or wetting agent; c) a metal containing salt, and d) an acidic pH adjusting agent effective to adjust the pH of the composition to a pH of between 2.5 and 5 when wetted on grass. The dry composition may be a granular composition, and may be applied by broadcasting over a large area.

11 Claims, No Drawings

SOLID MOSS CONTROL COMPOSITION

REFERENCE TO RELATED APPLICATIONS

This application is a continuation of U.S. application Ser. No. 12/169,314, filed Jul. 8, 2008 now abandoned, which is a continuation-in-part of U.S. application Ser. No. 09/532,687 (now U.S. Pat. No. 7,396,801), filed on Mar. 22, 2000, which is hereby incorporated by reference in its entirety.

FIELD OF THE INVENTION

The present invention relates to the field of chemical compositions to control or eradicate moss growing in lawns, golf course putting greens and other locations where moss is undesirable.

BACKGROUND OF THE INVENTION

Moss grows in many undesirable areas including lawns, golf course putting greens, other landscaped areas, and on structures such as walls, building foundations, monuments, and the like. Moss growing on structures is relatively easy to control using harsh chemicals, but moss is particularly hard to control or eradicate is areas that also contain desirable plants such as grasses. As a result, moss is a growing concern among homeowners, professional landscapers, and golf course superintendents.

Moss growing amongst grass and other desirable plants is a major concern for a number of reasons. Foremost among these is that moss detracts from the attractiveness of well-maintained lawns and other landscaped areas. Moss also tends to retain moisture and can decrease the usefulness of a lawn area. Additionally, under certain conditions, moss tends to spread easily and will crowd out other desirable plants, especially grasses.

Moss is a photosynthesizing terrestrial plant. Mosses are non-vascular plants so they need to be in contact with water to avoid drying out. Many mosses absorb water over their entire surface area and they are generally adapted to shady, moist locations. However, some mosses can survive long periods of desiccation (sometimes several years) and can withstand high temperatures in a dormant state. Laboratory studies have shown that mosses can tolerate dehydration levels equal to 80% of original biomass. When mosses are rehydrated, an immediate respiratory burst occurs, but recovery is slow.

While we have used the term "moss" in a generic sense, it has been reported that thousands of species of mosses exist. Moss can develop and thrive in many different environments, but areas that have poor soil conditions, lots of shade, and are damp tend to be the best for moss growth. Many of the moss varieties are known to infest home lawns, but the types that are known to infest golf course putting greens are more limited in number. In particular, it has been found that there are four moss varieties that often inhabit golf course putting green turf. They are *Byrum argentums, Byrum lisae, Amblystegium trichopodium*, and *Brachythecium* spp (Happ, K., USGA Green Section Record, September 1998). *Byrum argentum* (or silvery thread moss) is found in open sites and is one of the most common contaminants of putting green turf. It can generally be easily distinguished from other mosses because of its silvery appearance.

The presence of moss on putting greens is a special problem because of the unique conditions found in these areas. Golf course superintendents are faced with many turf management decisions, most of which are centered on providing the best possible playing conditions. This usually involves mowing the putting green grass (typically a short growing bentgrass variety) as short as reasonably possible. The shorter the putting green grass is, the faster the ball tends to travel. Faster putting surfaces tend to be the most desirable among golfers. Consequently, the health of putting green turf is compromised in order to deliver the desired playing effect.

Seeking maximum surface performance by cutting the greens short can lead to reduced bentgrass vigor. The shorter the greens are cut and the lower the bentgrass vigor, the better the conditions are for moss development and growth. A small moss colony can proliferated and turn into a bigger problem that is more difficult to overcome. One reason that moss on bentgrass putting greens proliferates is because of re-infestation by golfers and greens maintenance equipment that inadvertently carry the spores to new locations. If conditions remain favorable for moss growth, the moss can spread across a putting surface and severely lower playing conditions. The challenge for golf course superintendents is to eliminate moss infestation without compromising the health of putting green surfaces.

Despite these problems, the solutions for controlling or eradicating moss from lawns, golf course putting greens, and similar areas has remained rather limited and unsatisfactory. A few products exist that have been used to control moss to some extent, but to our knowledge there are no commercially available products that effectively kill moss over a broad area without damaging the turf. These products are typically powdered forms of certain metallic salts such as iron, zinc, and copper-sulfur compounds. They provide varying degrees of success, but also have significant drawbacks. Such powdered compositions are generally used only for spot treatment as they are difficult to apply over a broad area. While they can sometimes be put into solution, the concentration required to kill the moss colonies tends to be harmful to the grass. Additionally, a liquid product called DeMoss™ sold by Mycogen Corporation that is advertised as a moss control product. This product is a potassium salt of fatty acid.

In addition to the above, U.S. Pat. No. 5,139,561 to Talbot and Cooper discloses a method for protecting growing plants, including grasses, from fungal or microbial pathogens using a composition containing tetrakis (hydroxymethyl) phosphonium salt. One particular application of the composition is for control of mosses in lawns.

U.S. Pat. No. 4,276,732 to Nielsen discloses a device for killing moss on rooftops. In one embodiment, the device comprises a trough made of a layer of lead and copper. As rainwater filters through holes in the trough, an electrolytic action occurs in which ions of the metals dissolve into the water. The resultant aqueous electrolyte kills moss growing on the roof.

U.S. Pat. No. 5,009,700 to Rothgery describes a process for ridding moss from unwanted locations such as lawns, walls, monuments, building foundations, tombstones, and the like. The process comprises contacting the moss growing in said unwanted locations with an effective amount of a pyrithione salt. The composition optionally includes a surfactant or wetting agent.

U.S. Pat. No. 5,108,481 to Shutt discloses a method of making a palletized ferrous sulfate. It is further disclosed that the pelletized ferrous sulfate may be used as a moss-control agent.

U.S. Pat. No. 3,964,893 to Everingham and Hoenke teaches a lawn moss control composition comprising a granular ferric ammonium sulfate-ammonium sulfate double salt. The patent further discloses that the ferric double salt is as effective as ferrous ammonium sulfate for promoting the greening of turf grass.

U.S. Pat. No. 5,589,229 to Howard discloses a composition and method for preventing moss growth on roofs. The composition is an aqueous solution containing sodium oxide, silicon dioxide and a surfactant that is sprayed on the surface to be protected from moss growth. U.S. Pat. No. 4,936,898 to Nielsen discloses a method for killing moss growing on a surface by using a moss-killing powder containing an atomized elemental metal which slowly dissolves with water to form a biocidal solution which kills the moss. The powder is essentially a mixture of elemental zinc and copper mixed with a powdered carrier such as silica clay.

In addition to these commercial and/or patented chemical methods, manual methods of moss removal from grass are commonly used. For example, a non-chemical method for the control of moss in lawns is to rake out the moss, fertilize the ground, and re-seed with grass. This raking method is time consuming and hard on the grass. This method and other manual methods of moss removal can not be accomplished without also damaging the lawn. Accordingly, it would be desirable to provide a simpler moss treatment method that selectively eradicates moss in a lawn, golf course putting green, or other area, without harming the co-located grasses.

None of the known commercial products or the products described in the patent literature is fully satisfactory in meeting the current needs of homeowners, professional landscapers, and golf course superintendents. The present inventor has discovered a composition that more fully meets those needs by providing a convenient and effective moss control composition that does not damage grasses.

SUMMARY OF THE INVENTION

In one embodiment of the present invention there is provided a method of controlling moss comprising applying to grass infested with moss a dry composition comprising:
 a. a source of nitrogen,
 b. a non-ionic surfactant or wetting agent,
 c. a metal containing salt, and
 d. an acidic pH adjusting agent effective to adjust the pH of the composition to a pH of between 2.5 and 5;
 wherein said metal containing salt is applied in an amount of 0.1 to 80 ounces by weight per 1000 square feet of treatment area.

The inventive method may be used for controlling or eradicating moss in lawns, golf course putting greens, and other similar landscaped or turf containing areas. The inventive method is more effective than spot treating and will not harm the grass in the treatment area. Moreover, the inventive moss controlling compositions can be conveniently applied to a broad area needing treatment, such as by spraying or broadcasting using conventional spraying or broadcasting equipment.

The compositions used in the present invention eradicate moss while providing fertilizer to the grass so that it can reclaim areas taken over by the spreading moss. During treatment the turf may take on a dark green or blackish appearance due to the fertilizer and the iron sulfate in the product. The effect of the treatment is dramatic and the moss colonies begin to experience a desiccating effect and the turf quickly encroaches the moss colonies. The first signs of the decaying moss are exhibited by a blackish coloration.

The present invention may be an aqueous or a solid composition comprising: (1) fertilizer, (2) a surfactant or wetting agent, and (3) a metal containing salt. Additionally, the composition may optionally contain an acidic pH-adjusting ingredient.

When the composition of the present invention is applied to lawns and golf course putting greens, it has been surprisingly found that the moss is effectively eliminated after only a few treatments without damage to the grasses growing in the treated areas. The foregoing and other features and advantages of the invention will become apparent from the following detailed description of several embodiments of the invention.

DESCRIPTION OF PREFERRED EMBODIMENTS

One embodiment of the present composition provides a dry or aqueous product for spraying or broadcasting on lawns and putting green. The composition preferably comprises a fertilizer, a surfactant or wetting agent, and a metal containing salt. In both the aqueous and the dry embodiments the composition may optionally contain an acidic pH adjusting ingredient.

The compositions used in the present invention may include any source of nitrogen, including nitrogen-containing fertilizers, that provides sufficient nutrients to enhance grass vigor during the moss eradication treatments. Preferred fertilizers contain a high concentration of nitrogen. Such fertilizers are commonly known to those skilled in the art of turf maintenance. Some non-limiting preferred liquid fertilizers include Coron™ by Helena Chemicals and an isobutylenediurea (IBDU) fertilizer by Parex/Lebanon Seaboard Company. The amount of nitrogen included in the composition is such that about 0.1 to 8 pounds of fertilizer (as nitrogen) is applied per 1000 square feet of treatment area. A preferred range is 0.1 to 5 pounds of nitrogen applied per 1000 square feet of treatment area, with the range of 0.1 to 3 pounds being more preferred. In another preferred embodiment the range is 0.5 to 3 pounds of nitrogen per 1000 square feet of treatment area. However, it is understood by the skilled individual that the optimum amount of each of the ingredients will be determined by the conditions of the treatment surface including the variety of the grass(es) growing in the treatment area.

In one preferred embodiment, a slow-release nitrogen containing fertilizer is used. One particular example of such a fertilizer is isobutylenediurea (IBDU) supplied by Parex/Lebanon Seaboard Company.

In some embodiments the source of nitrogen is a potassium-free fertilizer. The presence of phosphorus in the composition is optional in some embodiments.

The type of surfactant or wetting agent used in the present invention is limited only in the sense that it must provide the composition with the ability to sufficiently wet the surface of the moss in order to enhance the biocidal action of the solution. Anionic, cationic, and non-ionic surfactants will all work in the present invention. Such surfactants are commonly known to the skilled artisan and do not need to be repeated in detail here.

The amount of surfactant or wetting agent used in the present invention can also vary widely with the major requirement being only that the composition contains an amount sufficient to wet the moss surface enough to enhance the killing effect of the other ingredients. However, in general the amount of surfactant or wetting agent included in the composition is sufficient to provide from 5 to 100 ounces of surfactant per 1000 square feet of surface treated. In a preferred embodiment the range is 5 to 50 ounces, and more preferably is 5 to 25 ounces applied per 1000 square feet of treatment area. The optimum amount of surfactant to use will be determined by, among other things, the type of surfactant, the variety of grass and moss and other conditions of the treatment area.

In a preferred embodiment, a non-ionic wetting agent is used. We have found Aqueduct™ and Primer™ 604 liquid non-ionic wetting agents from Aquatrols, Chemy Hill, N.J. to be highly effective. The Aqueduct™ product comprises a 50% blend of non-ionic polyols, 5% 1,2 propanediol, and 45% water. The Primer® 604 product is 95% polymeric polyoxyalkylenes and 5% oxoalkenyl hydroxy polyoxyalkane diyl.

In one embodiment a metal-containing salt is included in the composition. In some embodiments the metal-containing salt is any metal salt that exhibits a killing or desiccating effect on growing moss. Non-limiting examples of such salts include iron, copper, zinc, and magnesium containing salts. The second component of the salt may be a phosphate, a halide, or a sulfate. In one preferred embodiment, the salt is a metal sulfate and in an especially preferred embodiment, the salt is ferrous sulfate. In other embodiments the salt is an iron chloride or a magnesium chloride. In other embodiments the metal salt is a metal sulfate, a metal halide, or a metal phosphate, The amount of metal salt in the present invention is an amount sufficient to inhibit the growth or spread of the moss in the turf but less than an amount that will kill or severely harm other desirable plants (e.g. grasses) growing in the treatment area. Preferably the amount is sufficient to kill most of the moss after only a few treatments without harming the turf. The amount used will depend on the specific metal salt used, and on the variety of grass(es) in the treatment area because some varieties are more sensitive than others. In general, the amount of the metal salt will be within the range of 1 to 100 ounces (by weight) applied per 1000 square feet of treatment area. A preferred range of metal salt is 5 to 80 ounces, and in an even more preferred embodiment, the amount lies within the range of 5 to 50 ounces applied per 1000 square feet of treatment area. Most preferably, about 20 to 35 ounces of metal salt is used per 1000 square feet of treatment area.

Optionally, an acidic pH-adjusting agent is included in the composition of the present invention. The amount of this ingredient is not selected such that the pH of the composition when wetted by rain or watering on the grass is in the range of 2 to 6, more preferably in the range of 2.5 to 5 and most preferably in the range of about 3 to about 4. The pH will depend, of course, on the amount of water added to the dry composition, but the composition is generally formulated to work under normal rain and watering conditions for grass.

The pH-adjusting agent may be a weak acid in an amount effective to moderately lower the pH of the wetted composition as described above. Acids of the types known as mineral acids, organic acids, or Lewis acids can be used. Some non-limiting examples include: hydrochloric acid, phosphoric acid, citric acid, acetic acid, and tartaric acid. In one embodiment, dried acetic acid (vinegar) is used.

Additionally, it should be noted that the composition can contain other common ingredients to enhance the appearance and/or performance of the product. Such ingredients are known to those skilled in the art of agricultural or turf management chemical compositions. Some examples include suspending agents and similar ingredients to enhance the shelf life of the product, non-nitrogen containing fertilizers, insecticides, colorants, fragrances, solvents, thinning agents, and thickening agents to give a few non-limiting examples.

Further, in the liquid embodiments of the present invention the composition may be provided to the consumer in a diluted ready-to-use form, or it may be provided in a concentrated form needing dilution with water by the end-user. Additionally, the product can be supplied in two or more parts to the consumer to be mixed and/or diluted by the consumer prior to use. The latter form of the invention may be done to enhance the shelf of the product since some metal salts do not stay suspended very well in liquid composition.

The invention will now be described in the following illustrative examples. The examples are given for illustrating preferred embodiments of the invention and are not meant to be limiting in any way of the scope of applicant's invention.

Example 1

A test of the inventive methods and compositions was conducted on a sand-based putting green at the Joseph Valentine Turfgrass Research Center at The Pennsylvania State University, University Park, Pa. The green was a stand of Pennlinks™ creeping bentgrass (*Agrostis palustris*) and *Poa annua* mowed at 5/32 of an inch (bench setting) with a triplex mower. The green was fertilized, watered, and treated with pesticides to maintain acceptable turf quality prior to the study.

The test site selected had a good moss population ranging in size from 1/8 inch diameter up to 3 inch diameter colonies. Cultural practices such as aerating, spiking, and verticutting were not performed during the study to prevent mechanical injury and stress to the moss. The experimental design was a randomized complete block design replicated three times. Each individual plot was 3 by 10 feet. An initial moss count was taken on June 24 to determine the amount of moss in each plot. Each of the formulations were liquid and sprayed using a $CO_2$ powered walk behind sprayer equipped with a three-foot boom, and TeeJet 8008 flat fan nozzles. The sprayer was calibrated to deliver 4 gal./1000 sq. ft. The sprayer was rinsed out between each treatment. One of the nine formulations (seen Table 1) was applied to each of the twenty-seven plots. A total of five applications were made to each plot at about two week intervals. The applications began on June 23 and a final application was made on August 20. The final moss count was taken on September 18 (29 days after the final application).

TABLE 1

Moss Control Formulation in Experiment 1

| Formula | Components | Amount Applied (/1000 sq ft.) |
|---|---|---|
| 1 | Acid | 38.2 oz. |
| 2 | Ferrous Sulfate | 33.3 oz. |
| 3 | Acid + Ferrous Sulfate | 38.2 oz.; 33.3 oz. |
| 4 | Acid + Fertilizer | 38.2 oz.; 2/3 lb. N |
| 5 | Acid + Fertilizer + Wetting Agent | 38.2 oz.; 2/3 lb. N; 14.5 oz. |
| 6 | Ferrous Sulfate + Fertilizer | 33.3 oz.; 2/3 lb. N |
| 7 | Ferrous Sulfate + Fertilizer + Wetting Agent | 33.3 oz.; 2/3 lb. N; 14.5 oz. |
| 8 | Acid + Ferrous Sulfate + Fertilizer + Wetting Agent | 38.2 oz.; 33.3 oz.; 2/3 lb. N; 14.5 oz. |
| 9 | Control (untreated) | N/A |

The acid used was a 5% by volume solution of acetic acid (vinegar). The ferrous sulfate was a fine grade ferrous sulfate powder supplied by Agway. The fertilizer used was a sprayable IBDU 30-0-0 formulation from Lebanon Seaboard and the wetting agent used was a non-ionic Aqueduct™ made by Aquatrols, Inc. The entire composition was diluted so that four gallons of composition would contain the amounts specified in Table 1. The composition was applied at a rate of four gallons per 1000 square feet of treatment area.

It was observed that Formulations 2, 3, 6, 7, and 8 darkened the turf color because of the ferrous sulfate component in those composition. This condition lasted for two to three days. Moss color in these plots turned black following application, but began to "green-up" at the surface prior to the next application. With each subsequent application, the moss turned black again and less moss recovered. Additionally, it was qualitatively noticed that formulations with the fertilizer component stimulated turf growth, which aided in the turfs ability to fill in the voids left by the eradicated moss.

Table 2 shows the results of the experiment by the average reduction in the number of moss colonies larger than about 1/8 of an inch. The average was taken across three plots for each formulation. For formula 8 it was observed that moss infections of about 3/4 of an inch and smaller were completely eliminated after three applications. More applications were required to eradicate moss colonies larger than 3/4 inch. Also, it was noted that as the summer progressed, there was a natural decline in the moss population as can be seen from the 25% reduction observed for the untreated plots. The plots that were sprayed with treatments that included fertilizer in the formulation were more dense, aggressive, and healthy. The best formulation was the composition containing acid, ferrous sulfate, fertilizer and wetting agent. This formulation nearly completely eradicated the moss from the plots.

TABLE 2

Reduction in Moss Populations

| Formula | Components | Average Moss Reduction |
|---|---|---|
| 1 | Acid | 74.3% |
| 2 | Ferrous Sulfate | 86.1% |
| 3 | Acid + Ferrous Sulfate | 77.3% |
| 4 | Acid + Fertilizer | 34.2% |
| 5 | Acid + Fertilizer + Wetting Agent | 49.1% |
| 6 | Ferrous Sulfate + Fertilizer | 91.9% |
| 7 | Ferrous Sulfate + Fertilizer + Wetting Agent | 91.2% |
| 8 | Acid + Ferrous Sulfate + Fertilizer + Wetting Agent | 98.5% |
| 9 | Control (untreated) | 25.3% |

Example 2

A second test was performed to qualitatively test the safety and effectiveness of the present invention on a large variety of bentgrasses. This test was performed on the creeping bentgrass putting green variety trial at The Pennsylvania State University's Joseph Valentine Turfgrass Research Center. The test area is over 12,000 square feet containing 125 different creeping bentgrass varieties. The bentgrass plots were mowed at a bench setting of 0.120 inch with a Toro 1000 walk behind greens mower. Also, there were three plots (measuring 4 feet by 6 feet each) for each of the 125 different varieties. Prior to the application of any product, it was observed that the entire area contained significant amounts of moss colonies ranging in size from small colonies under an inch in diameter to a few larger colonies measuring over 3 inches in diameter. A composition the same as formulation 8 in the previous example was applied to the entire area in two week intervals using a conventional golf course sprayer. After about 6 weeks and 3 applications, it was observed that the moss was well under control with a dramatic reduction in total moss count. Most of the smaller moss colonies had been completely eradicated. There were a few extremely large colonies which measured over 3 inches in diameter which took several more spot treatments to kill. Additionally we did not observe any damage to any of the varieties of grass in the study. We concluded from this study that the present invention is safe and effective when applied to a variety of turfs of the type commonly used on golf course putting greens.

As previously indicated, in some embodiments the composition is provided in a granular or other solid form to that the composition may be applied in dry form by, for example, broadcast application of the granules. Such dry embodiments may include:
 a. a source of nitrogen;
 b. a non-ionic surfactant or wetting agent,
 c. a metal containing salt, and
 d. an acidic pH adjusting agent effective to adjust the pH of the composition when wetted on grass to between 2.5 and 5.

The source of nitrogen may be any source of nitrogen described above, although it will be provided in dry form. In one preferred embodiment the dry composition includes a commercial available nitrogen source, such as, for example, urea, diureas, methelene ureas, ureaforms, coated ureas, urea condensations, nitrates, ammonia, and isobutylenediurea. In some embodiments an organic source of nitrogen is used.

The surfactant or wetting agent may be any surfactant or wetting agent discussed above, although it will be in dry form.

The metal containing salt may be any of the metal salts discussed above, including preferably an iron-, copper-, zinc-, or magnesium-containing phosphate, halide, or sulfate. In preferred embodiments the metal sulfate is selected from the group consisting of copper sulfate, zinc sulfate, iron sulfate, iron chloride, and magnesium chloride.

The pH adjusting agent is effective for reducing the pH of the composition when wetted on grass, as described above. As previously indicated, the pH-adjusting agent preferably comprises a dry form of one or more members selected from the group consisting of hydrochloric acid, phosphoric acid, citric acid, acetic acid, and tartaric acid;

In other embodiments there is provided a method of controlling moss with a dry, granular formulation. That method may comprise applying to grass infested with moss a dry, granular composition comprising:
 a. a source of nitrogen,
 b. a non-ionic surfactant or wetting agent,
 c. a metal containing salt, wherein said metal salt is a metal sulfate or metal phosphate, and
 d. an acidic pH adjusting agent effective to adjust the pH of the composition when wetted on grass by normal rain or watering to a pH of between 2.5 and 5.

The metal containing salt may be a metal sulfate. In one embodiment the metal sulfate is selected from the group consisting of copper sulfate, zinc sulfate, and iron sulfate.

The dry formulations may include the same non-ionic wetting agent(s) as the aqueous compositions described above, including, but not limited to, metal containing sulfates or phosphates. The dry formulations may also include the same pH-adjusting agents as were used with the aqueous compositions, including, but not limited to, one or more members selected from the group consisting of hydrochloric acid, phosphoric acid, citric acid, acetic acid, and tartaric acid. Both the non-ionic wetting agent and the pH-adjusting agents may be provided in dry form.

It is also to be appreciated that some of the ingredients may be coated with a polymer or plastic to keep them from reacting with other ingredients in the mixture while stored. For example, urea nitrogen may be coated to keep it from reacting with the iron or other sulfates while on the shelf.

The dry compositions may be provided as granules. The granule size is preferably between 20 mesh and 200 mesh, with granule sizes of 50-150 mesh being more preferred and granule sizes of about 100 mesh being most preferred. Fine powders are to be avoided in most embodiments.

Example 3

A dry, granular formulation was prepared using the components previously used in liquid formulation testing. As before, the grass was fertilized, watered, and treated with pesticides to maintain acceptable turf quality prior to the study. The test site had a good moss population ranging in size from ¼ inch diameter up to 3 inch diameter colonies. Cultural practices such as aerating, spiking, and verticutting were not performed during the study to prevent mechanical injury and stress to the moss.

The fertilizer used was a granular IBDU formulation from Lebanon Seaboard. The acid used was a dry acetic acid, and the metal salt was ferrous sulfate, in an amount effective to provide 32 ounces of metal salt per 1000 feet of treatment area. The wetting agent was a non-ionic Pluronic™ surfactant made by BASF. The individual granules were coated with clay, wax, or polymer to keep the individual components separate during storage and to regulate the release rate of the composition when applied to wet grass. The individual particles were all about the same weight so that they broadcast evenly from the spreader.

It was observed that the granular formulation darkened the turf color because of the ferrous sulfate component in the composition. This condition lasted for two to three days. Moss color in these plots turned black following application, but began to "green-up" at the surface prior to the next application. With each subsequent application, the moss turned black again and less moss recovered. Additionally, it was qualitatively noticed that formulations with the fertilizer component stimulated turf growth, which aided in the turfs ability to fill in the voids left by the eradicated moss. The moss reduction was greater than 90% in the area tested.

Although the invention has been described in detail in the foregoing embodiments for the purpose of illustration, it is to be understood that such detail is solely for that purpose and that variations can be made therein by those skilled in the art without departing from the spirit and scope of the invention except as it may be limited by the claims.

What is claimed is:

1. A method of controlling moss, comprising applying to grass infested with moss a dry composition comprising:
    a. coated granules of a source of nitrogen, wherein said source of nitrogen comprises a member selected from the group consisting of urea, diureas, methylene ureas, ureaforms, urea condensations, nitrates, ammonia, and isobutylenediurea; and wherein said granules are coated with a clay, a wax, or a polymer coating;
    b. coated granules of a non-ionic surfactant or wetting agent, wherein said granules are coated with a clay, a wax, or a polymer coating,
    c. coated granules of a metal containing salt, wherein said metal containing salt comprises a member selected from the group consisting of iron-, copper-, zinc-, or magnesium-containing phosphates, halides, or sulfates, and wherein said granules are coated with a clay, a wax, or a polymer coating, and
    d. coated granules of an acidic pH adjusting agent effective to adjust the pH of the composition to a pH of between 2.5 and 5 when wetted on grass by normal amounts of rain or watering, wherein said granules are coated with a clay, a wax, or a polymer coating.

2. The method of claim 1 wherein the metal containing salt is a metal sulfate.

3. The method of claim 2 wherein the metal sulfate is selected from the group consisting of copper sulfate, zinc sulfate, iron sulfate, and iron chloride.

4. The method of claim 1 wherein the metal containing salt is applied in an amount of 20 to 50 ounces by weight per 1000 square feet of treatment area.

5. The method of claim 1 wherein the pH-adjusting agent comprises a member selected from the group consisting of hydrochloric acid, phosphoric acid, citric acid, acetic acid, and tartaric acid.

6. The method of claim 1 wherein said applying is by broadcasting.

7. The method of claim 1 wherein the source of nitrogen is methylene urea.

8. The method of claim 1 wherein the non-ionic surfactant comprises 95% polymeric polyoxyalkylenes and 5% oxoalkenyl hydroxy polyoxyalkane diyl.

9. The method of claim 1 wherein the metal containing salt is iron sulfate.

10. The method of claim 1 wherein the acidic pH adjusting agent is citric acid.

11. The method of claim 1 wherein the source of nitrogen is methylene urea, the non-ionic surfactant comprises 95% polymeric polyoxyalkylenes and 5% oxoalkenyl hydroxy polyoxyalkane diyl, the metal containing salt is iron sulfate, and the acidic pH adjusting agent is citric acid.

* * * * *